United States Patent [19]

Krutchen et al.

[11] Patent Number: 4,573,345

[45] Date of Patent: Mar. 4, 1986

[54] MELT RHEOMETER CONTROL

[75] Inventors: Charles M. Krutchen, Pittsford; Raj Ranjan, Fairport; Jan-Chin Yang, Pittsford, all of N.Y.

[73] Assignee: Mobil Oil Corporation, New York, N.Y.

[21] Appl. No.: 630,155

[22] Filed: Jul. 12, 1984

[51] Int. Cl.⁴ ............................................ G01N 11/04
[52] U.S. Cl. ..................................................... 73/56
[58] Field of Search ............................... 73/56, 55, 54

[56] References Cited

U.S. PATENT DOCUMENTS

| | | | |
|---|---|---|---|
| 3,048,030 | 8/1962 | De Haven | 73/56 |
| 3,116,630 | 1/1964 | Piros | 73/55 |
| 3,138,950 | 6/1964 | Welty et al. | 73/56 |
| 3,360,986 | 1/1968 | Rothschild | 73/56 |
| 3,952,577 | 4/1976 | Hayes et al. | 73/55 |
| 4,241,602 | 12/1980 | Han et al. | 73/56 |
| 4,425,790 | 1/1984 | Bice et al. | 73/55 |
| 4,449,395 | 5/1984 | Kurtz et al. | 73/56 |

Primary Examiner—Stewart J. Levy
Assistant Examiner—Hezron E. Williams
Attorney, Agent, or Firm—Alexander J. McKillop; Michael G. Gilman; Charles J. Speciale

[57] ABSTRACT

A method for measuring the viscosity of a foamable plastics melt where accurate readings are difficult because of the melt material beginning to foam while in the rheometer test section slit. The pressure on the melt is elevated above the foaming point and maintained at an elevated level during the entire time during which the melt sample is diverted through the rheometer.

3 Claims, 2 Drawing Figures

MELT RHEOMETER CONTROL

BACKGROUND OF THE INVENTION

1. Field of the Invention

This invention relates generally to rheometers and more particularly to on-line rheometers that provide analysis of the viscosity of a product, particularly such as a foamable plastics product, in a manner adaptable to computer control to optimize manufacturing conditions. During the manufacture of a foamable plastics material, such as polystyrene, there is a good deal of waste which is in turn chopped up for recycling and mixing with virgin material. Since the viscosity of recycled material varies, it also introduces variations in the viscosity of the foamable resin mix, leading to difficulty in producing uniform foam products. Thus, the viscosity must be continuously measured and controlled. The viscosity of resin mix may be controlled by the percentage of recycled material, the percentage of blowing agent and/or the melt temperature.

2. Description of the Prior Art

Rheometers, including rheometers that employ a restriction such as a slit or a capillary, are well known. Of special interest is U.S. Pat. No. 4,241,602 to C. D. Han and prior art identified therein, all of which is hereby specifically incorporated by reference.

SUMMARY OF THE INVENTION

It is an object of the present invention to provide a method of plastics melt viscosity monitoring and control in which it is possible to obtain accurate readings by preventing the foamable melt from foaming.

It is a further object to decrease the residence time in the rheometer in order to have a fast response measurement time and to lower the shear rate in order to have high sensitivity of apparent viscosity per unit of melt index. Since a small shear rate is usually accompanied by a long residence time, it is an object of the present invention to optimize the method by striking a compromise between residence time and shear rate.

It is a further object of this invention to optimize viscosity measurement conditions by use of a test section slit in the rheometer, where the cross-sectional area (width times height) is so configured that the width of the test section slit is at least ten times greater than the height.

It is another object of this invention to provide a method in which flow conditions in the rheometer are optimized to give maximum information of melt properties according to the following formula:

$$0.1 \leq Q/Wh^2 \leq 2$$

where
Q = volumetric flow rate (in$^3$/sec);
W = width of test section (in inches); and
h = height of test section (in inches).

DETAILED DESCRIPTION OF THE PREFERRED EMBODIMENT

Figure 2:
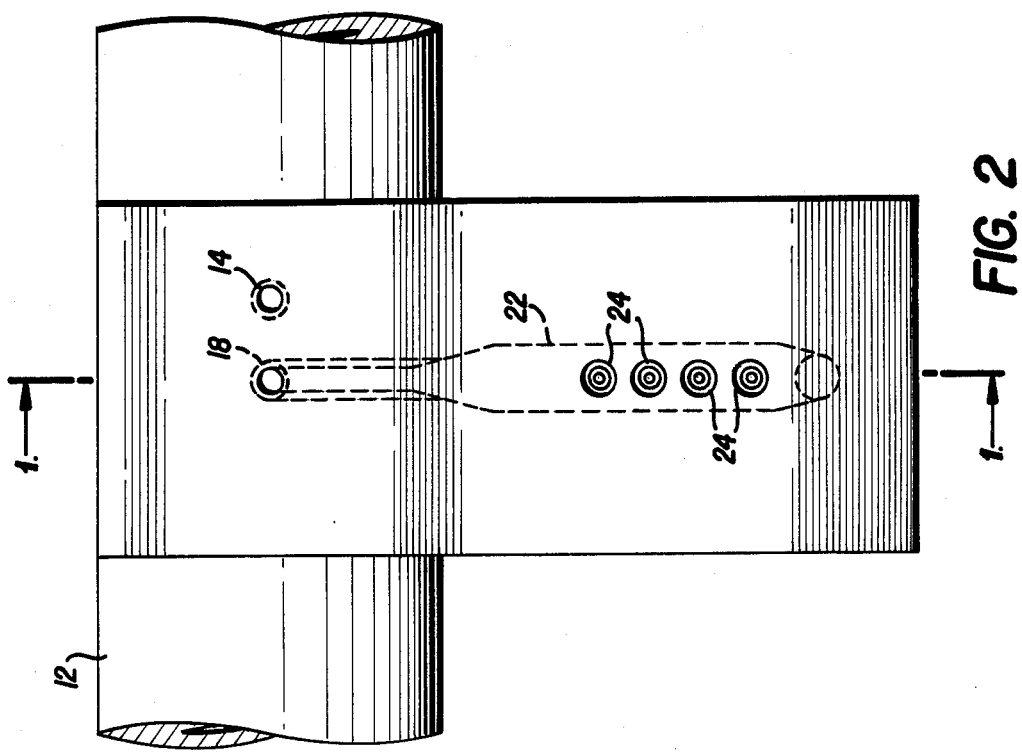
Figure 1:
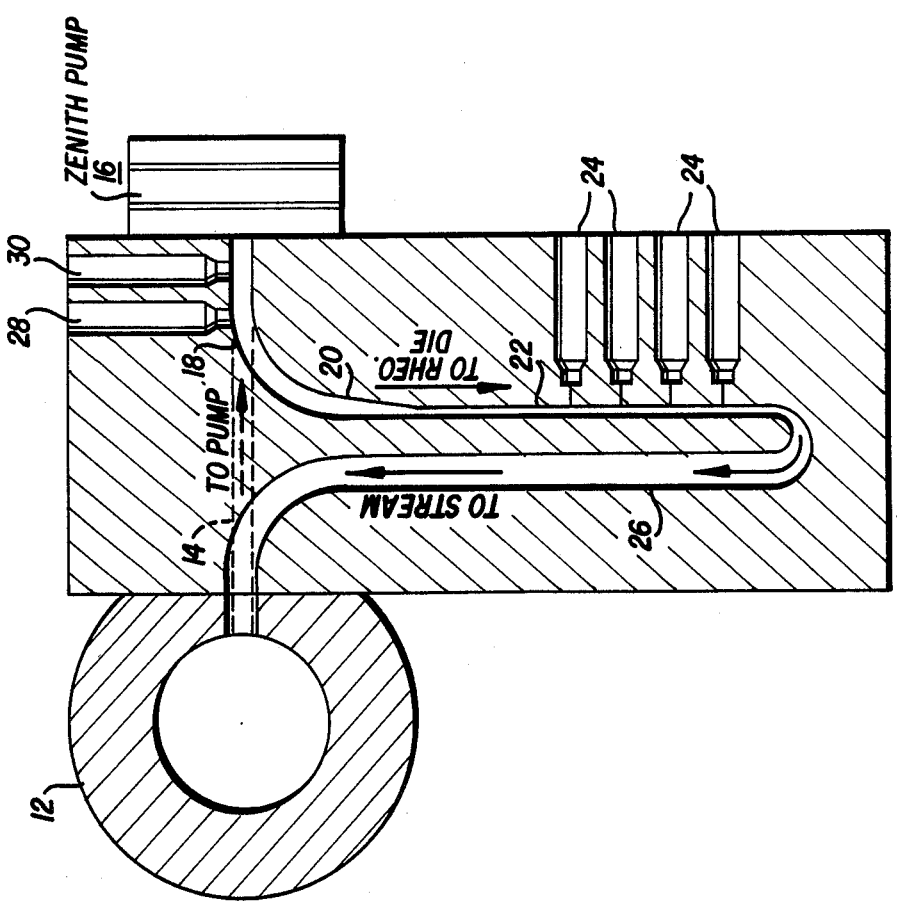
FIG. 1 is a cross-sectional view taken along line 1—1 of FIG. 2 showing the test section slit of a rheometer, the transducers adjacent the slit and the slit inlet and exit conduits; and, FIG. 2 is an elevational view looking from the left-hand side of FIG. 1.

Referring now to FIG. 1, a supply adaptor 12 feeding the main die of a plastics extrusion apparatus carries plastics melt under sufficient pressure to prevent foaming thereof, the melt moving in a direction outwardly from the surface of the drawing of FIG. 1. A small sample (about 0.4-0.5 lb/hr) of that plastics melt flow is diverted into a conduit 14 to supply a pump 16. This pump, such as a Nichols/zenith metering pump Type HBP-5557, 0.160 cc/rev, is driven so as to increase the pressure sufficiently to drive the melt back into the adaptor. Under these conditions, the melt will not foam in the test section 22. The pump is preferably turned between 10 and 60 RPM's and, in one preferred embodiment, at about 20 RPM. The plastics melt, which is maintained, in one instance, at a temperature of about 300° F., passes through inlet conduit 18, through transition section 20 and into test section slit 22. A plurality of transducers 24 then sense the pressure along this slit and that data, fed into a microprocessor, is used to compute the shear rate and thus the viscosity of the melt passing therethrough. U.S. Pat. No. 4,241,602 discloses a means and method for calculating the viscosity.

The cross-sectional area of the slit 22, width times height (both measured in inches), must be such that the width of the test section is at lest ten times greater than the height. In a preferred embodiment, the width equals 0.700 inches, the height 0.070 inches and the length 4.0 inches. The length is not critical, but must be such that the pressure transducers 24 will read pressure drop in a region where the pressure drop is linear, that is away from entrance or exit effects. Although four transducers are shown in the illustrated embodiment, it is contemplated that in a production line installation which is used consistently for the same type of material, a lesser number of transducers would suffice, for example, two transducers which are positioned to avoid entrance and exit effects.

In the passage of the melt from the adaptor (12) through the pump and the test section, it is necessary to keep the residence time of the melt to a minimum to facilitate computer control of the extrusion process. Specifically, it is desirable to adhere to the following residence time parameter $$RT = V/60Q \leq 5 \text{ minutes}$$

where
RT = Residence Time (in minutes);
Q = Volumetric Flow Rate (in$^3$/sec); and
V = Total Volume of Sections 14, 18, 20 and 22 (in$^3$).

After leaving the test section slit 22, the plastics melt passes through exit conduit 26 and is ultimately returned to adaptor 12 at a location downstream from entrance conduit 14.

A pressure transducer 30 and a melt thermocouple 28 are connected to the microprocessor and located adjacent the exit of the pump 16 to monitor the pressure and the melt temperature. These are connected into the microprocessor so as to maintain complete monitoring of the melt throughout its cycle in the rheometer.

An important aspect of the present method is to divert a sample from the adaptor 12 and to elevate it to a pressure, by means of pump 16, to a sufficiently high level so that no foaming of the melt will take place. Obviously if the melt were to foam in the rheometer, particularly when passing through slit 22, the effect would be to destroy the accuracy of any viscosity readings obtained therefrom. It is also important that the pressure be maintained at a high enough level so that the discharge from the rheometer, passing through conduit 26, can be injected back into adaptor 12 without difficulty. The viscosity of the melt must be measured when the blowing agent is in solution and it is thus necessary to keep the pressure high enough to prevent foaming while all measurements are being taken.

The method of the present invention utilizes an increased pressure in the test sample and passes the sample through a test section slit of the above-described cross-section. This leads to a decreased residence time, an acceptable shear rate, and prevents foaming within the rheometer, thus assuring accurate viscosity measurement and control. Obviously, modifications and variations of the present invention are possible in light of the above teachings. Thus, it is to be understood that within the scope of the following claims, the invention may be practiced in a manner other than specifically described above.

We claim:

1. A method of measuring the viscosity of a foamable plastics melt comprising:

diverting a test sample of said plastic melt from the supply feed to an extrusion die;

elevating the pressure of said melt sample to a level higher than that said supply pressure and sufficiently high to prevent foaming of said melt;

continuously passing said pressurized melt sample through an elongated test section of a rheometer with a minimum residence time;

maintaining the pressure on said melt sample while continuously passing through said test section at a known shear rate and at a pressure level sufficiently high to prevent foaming of the melt sample;

measuring the pressure on said melt sample while passing through said test section at at least two separate locations which are spaced apart along the length thereof;

computing the viscosity of said melt by comparison of said measured pressures.

2. The method of claim 1, including decreasing the residence time and lowering the shear rate by passing the melt through an elongated test section having a cross-section such that its width is at least 10 times greater than its height.

3. The method of claim 1, including the shear rate range of $0.1 \leq Q/Wh^2 \leq 2$ and the residence time range of $V/Q \leq 5$ minutes.

* * * * *